United States Patent
Elder et al.

(10) Patent No.: US 6,316,500 B1
(45) Date of Patent: Nov. 13, 2001

(54) ALIPHATICALLY UNSATURATED HYDROXY BENZOATES AND PRESERVATIVE COMPOSITIONS THEREOF

(75) Inventors: Todd Elder, Rockaway; John J. Merianos, Middletown, both of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/225,629

(22) Filed: Jan. 5, 1999

(51) Int. Cl.$^7$ .............................. A01N 37/10; C07L 64/88
(52) U.S. Cl. ................................. 514/544; 560/67
(58) Field of Search ................ 514/544; 560/67

(56) References Cited

FOREIGN PATENT DOCUMENTS

320032 * 6/1989 (EP).

OTHER PUBLICATIONS

Chem Abs/96:29920 of JP 56073006 Jun. 17, 1981.*

* cited by examiner

*Primary Examiner*—Paul J. Killos
(74) *Attorney, Agent, or Firm*—Marilyn J. Maue; William J. Davis; Walter Katz

(57) ABSTRACT

The hydroxybenzoate compounds of this invention are defined by the formula:

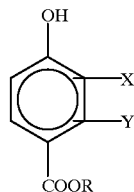

wherein Y is hydrogen, hydroxy, halo, a $C_1$ to $C_6$ alkyl or a $C_2$ to $C_6$ alkyl ether;

R is a $C_4$ to $C_6$ mono- or di-olefinically unsaturated hydrocarbon radical, a $C_4$ to $C_7$ mono- or di-acetylenically unsaturated hydrocarbon radical or a $C_2$ to $C_3$ acetylenically unsaturated hydrocarbon radical when at least one of X and Y is other than hydrogen and X is hydrogen, hydroxy, halo, a $C_1$ to $C_6$ alkyl, a $C_2$ to $C_6$ alkyl ether or

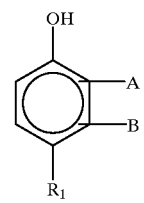

in which A is selected from the group of X,
B is selected from the group of Y and
$R_1$ is hydrogen, hydroxy, $C_1$ to $C_6$ alkyl, $C_1$ to $C_6$ alkoxy or —COOR$_2$ in which $R_2$ is $C_1$ to $C_6$ alkyl, a $C_2$ to $C_6$ olefinically unsaturated hydrocarbon radical or a $C_2$ to $C_7$ acetylenically unsaturated hydrocarbon radical.

The invention also pertains to food, beverage, cosmetic, agrichemical and topically applied pharmaceutical compositions containing an effective preservative amount of the hydroxy aliphatically unsaturated benzoate having the formula:

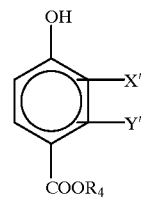

wherein X' is selected from the group of X; Y' is selected from the group of Y and $R_4$ is a $C_2$ to $C_6$ mono- or di-olefinically unsaturated hydrocarbon radical or a $C_2$ to $C_7$ mono- or di-acetylenically unsaturated hydrocarbon radical.

14 Claims, No Drawings

ALIPHATICALLY UNSATURATED HYDROXY BENZOATES AND PRESERVATIVE COMPOSITIONS THEREOF

BACKGROUND OF THE INVENTION

Various species of p-hydroxy benzoic acid esters and their salts have found use as preservatives for foods and beverages as is disclosed in U.S. Pat. Nos. 2,046,324; 2,056,176; 3,767,827; 4,366,171 and 4,568,382. Although some of these esters possess preservative properties over a broad spectrum of fungicides, they exhibit low solubility in water which limits their use. Other hydroxy benzoates are effective only against gram positive microorganisms and several of these esters produce residues which are harmful to humans or the environment; accordingly their continued use has been barred.

The foregoing drawbacks limit the selection of totally acceptable and effective fungicidal agents. Moreover, it has been found that closely related compounds exhibit quite different control abilities and microorganism selectivity. For example, heptyl p-hydroxybenzoate has been used at about 10 ppm as a beer preservative to kill saprogenous microorganisms; however it has limited solubility in beer so that the beer becomes turbid at about 0° C. Similar drawbacks are noted for the treatment of soy and other beverages.

To be commercially acceptable, the type of hydroxy benzoate must be moderately water soluble and leave no toxic residue, they should exhibit high activity at low concentrations against a broad spectrum of microorganisms and fungi and they must be economical to prepare and apply. Accordingly it is an object of this invention to achieve these aims in a hydroxy benzoate derivative which is modified so as to balance significantly improved water solubility with high anti microorganism and fungicidal activity against both gram positive and gram negative species. Another object of the invention is to provide non-toxic hydroxy benzoates by an economical and commercially feasible process. These and many other benefits of the invention will become apparent from the following description and disclosure.

THE INVENTION

In accordance with this invention there is provided new and useful hydroxy benzoates defined by the formula:

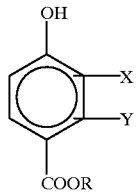

I wherein Y is hydrogen, hydroxy, halo, a $C_1$ to $C_6$ alkyl or a C2 to $C_6$ alkyl ether;
  R is a $C_4$ to $C_6$ mono- or di-olefinically unsaturated hydrocarbon radical, a $C_4$ to $C_7$ mono- or di-acetylenically unsaturated hydrocarbon radical or a $C_2$ to $C_3$ acetylenically unsaturated hydrocarbon radical when one or both of X and Y is other than hydrogen and
  X is hydrogen, hydroxy, halo, a $C_1$ to $C_6$ alkyl, a $C_2$ to $C_6$ alkyl ether or

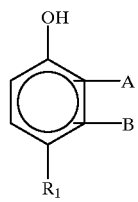

in which A is selected from the group of X,
  B is selected from the group of Y and
  $R_1$ is hydrogen, hydroxy, $C_1$ to $C_6$ alkyl, $C_1$ to $C_6$ alkoxy or —$COOR_2$ in which $R_2$ is $C_1$ to $C_6$ alkyl, a $C_2$ to $C_6$ olefinically unsaturated hydrocarbon radical or a $C_2$ to $C_7$ acetylenically unsaturated hydrocarbon radical.

Also in accordance with this invention there is provided food, beverage and cosmetic compositions containing an effective preservative amount of a hydroxy benzoates having the above formula except for substituent R, which in the case of the preservative composition for the above substances, can be a $C_2$ to $C_6$ olefinically unsaturated hydrocarbon radical or a $C_2$ to $C_6$ acetylenically unsaturated hydrocarbon radical.

The present hydroxy benzoates exhibit good anti-microbial and fungicidal activity for a broad spectrum of gram negative and gram positive substances which cause deterioration of beverage, food, drug and cosmetic products, including alcoholic and non-alcoholic beverages, such as beer, ale, wines, fruit juices, milk, etc., frozen and canned meat, vegetable and fruit food products, bread and pastries, shampoo, face and body lotions, hair rinses and conditioners, bath oils and the like. The present hydroxy benzoate preservative is preferably incorporated with such food, beverage, topically applied drug or cosmetic products in a concentration of between about 0.1 and about 1.5 wt. %, most preferably between about 0.2 and about 1 wt. %. In foods and beverages, less that 1 wt. % of the hydroxy benzoate is highly effective and can be incorporated as a water or aqueous solution.

The present hydroxy benzoates achieve significantly improved water solubility and high anti-microbial and fungicidal activity which is achieved by a controlled lipophilic/hydrophilic balance between the substituents on the aromatic ring. The activity of the present compounds extends over a broad spectrum to include control of both gram negative and gram positive microorganisms and fungi including *A. niger, B. cepacia, C. albicans, E. coli, P. aeruginosa, S. aureus, stephylococcus, salmonella, P. eugaris, S corepislac*, myxo- and eu-mycotina and other mycota and organisms affecting comestable and cosmetic products.

Particularly preferred among instant hydroxy benzoates are the propargyl dihydroxy benzoate, propargyl chloro hydroxy benzoate, 2,4-hexadienyl-4-hydroxy benzoate, 2,4-hexadienyl-2,4-dihydroxy benzoate, 1, 3-butadienyl-2,4-dihydroxy benzoate, 1,3-butadienyl-3-chloro-2,4-dihydroxy benzoate, 3-butynyl-2,4-dihydroxy benzoate, and 3-butynyl-4-hydroxy benzoate.

In each of the above benzoates, the lipophilic R group is selected to balance the remaining hydrophilic ring substituents, such as —OH, alkoxy, halo etc. It is now discovered that the activity of the preservative varies directly with the length of the hydrocarbon chain up to 6 carbon atoms in the R of the ester linkage; whereas the water solubility decreases and must be modified by selection of the hydrophilic ring substituents.

The hydroxy benzoates of this invention can be prepared by contacting reactant the hydroxy benzoic acid

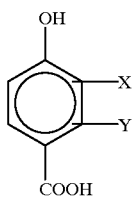

in the presence of an alkali metal hydroxide with a coreactant which is the halide of the R group in the above benzoate formula and in the presence of a condensing agent, e.g. dicyclohexylcarbamide, in a 1:1–1:1.5 benzoate to agent mole ratio. The reaction is carried out in at least 40 wt. % solution containing a suitable solvent such as an alcohol, e.g. isopropanol, an ether, dioxane, tetrahydrofuran, acetone, methylene chloride and the like.

Alternatively the benzoate can be prepared by reaction of the above hydroxy benzoic acid with the aliphatic alcohol coreactant corresponding to the R group in the above formula and in the presence of a condensing agent in a 1:1–1:1.5 benzoate to agent mole ratio. This reaction is also carried out in at least a 40 wt. % solution of a suitable solvent of the above group, excluding alcohol.

The mole ratio of reactant to coreactant in the above processes is generally between about 1:1 and about 2.5:1, preferably between about 1:1 and 1.5:1 and the esterification reaction is carried out under constant agitation and at reflux temperature, e.g. between about 400 and about 100° C., preferably between about 500 and about 70° C. over a period of from 2 to 24 hours, more often from 4 to 12 hours. The resulting solid reaction hydroxy benzoate product is then distilled or evaporated to remove solvent, extracted with for example methylene chloride followed by water washing and then dried.

The hydroxybenzoates of this invention exhibit good water solubility and preservative properties for foods, beverages, cosmetics, soaps, creams and lotions and other formulations, e.g. agrichemical and pharmaceutical formulations.

The hydroxybenzoates having the formula

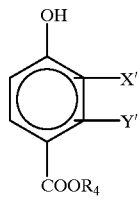

II wherein X' is selected from the group of X; Y' is selected from the group of Y and $R_4$ is a $C_2$ to $C_6$ mono- or di-olefinically unsaturated hydrocarbon radical or a $C_2$ to $C_7$ mono- or di-acetylenically unsaturated hydrocarbon radical; exhibit good water solubility and preservative properties for foods and beverages, cosmetic hair and skin care products such as, soaps, creams and lotions, pharmaceutical and agrichemical formulations including pesticides and fungicides as well as livestock pesticidal washes or dips.

When employed as a preservative, effective concentrations of the hydroxy benzoates of formula II in the above mixtures can vary from as little as about 0.001 up to about 2.0%. The hydroxybenzoates in the above concentrations are readily dissolved in liquid foodstuffs, condiments and alcoholic or non-alcoholic beverages and can be added in an aqueous solution in any stage of a formulation. Formulations of these hydroxybenzoates can also be employed with a surfactant, thickener or any of the excipients normally included with an active cosmetic component in a formulation. Thorough mixing at about room temperature provides a desired homogeneous product.

Having generally described the invention, reference is had to the following examples which illustrate the preferred embodiments but which are not to be construed as limiting to the scope of the invention as set forth in the appended claims.

METHODS FOR PREPARING THE HYDROXY BENZOATES

EXAMPLE 1

Propargylparaben p-Hydroxybenzoic acid (0.724 mole) and sodium hydroxide (0.724 mole) were dissolved in 50% isopropyl alcohol (400 ml). Propargyl bromide (0.724 mole) was added and the solution was heated to reflux for 6 hours. The solution was then cooled and the isopropyl alcohol was removed under vacuum. The residue was taken up in methylene chloride (200 ml), washed with water (200 ml), aturated sodium bicarbonate, saline and dried over magnesium sulfate. Removal of the solvent yielded crude product, which was recrystallized, from $CCl_4$ to give pure propargylparaben. (62.9% yield) m.p. 107–108° C.

EXAMPLE 2

Propargyl 3,4-Dihydroxybenzoate

Using the above procedure, 3,4-dihydroxybenzoic acid (0.0649 mole) and sodium hydroxide (0.0649 mole) were dissolved in 50% isopropyl alcohol (200 ml). Propargyl bromide (0.0649 mole) was added and the solution was heated to reflux for 6 hours. The solution was then cooled and the isopropyl alcohol was removed under vacuum. The residue was taken up in methylene chloride (200 ml), washed with water (200 ml), saturated sodium bicarbonate, saline and dried over magnesium sulfate. Removal of the solvent yielded crude product, which was recrystallized, from $CCl_4$ to give the pure product. (68.0% yield) m.p. 127–129° C.

EXAMPLE 3

Propargyl 2,4-Dihydroxybenzoate

Using the above procedure, 2–4-dihydroxybenzoic acid (0.01 mole) and sodium hydroxide (0.01 mole) were dissolved in 50% isopropyl alcohol (200 ml). Propargyl bromide (0.01 mole) was added and the solution was heated to reflux for 6 hours. The solution was then cooled and the isopropyl alcohol was removed under vacuum. The residue was taken up in methylene chloride (200 ml), washed with water (200 ml), saturated sodium bicarbonate, saline and dried over magnesium sulfate. Removal of the solvent yielded crude product, which was recrystallized, from $CCl_4$ to give the pure product. (26.6% yield) m.p. 104–106° C.

EXAMPLE 4

Propargyl 3-Chloro-4-Hydroxybenzoate

Using the above procedure, 3-chloro-4-hydroxybenzoic acid (0.0826 mole) and sodium hydroxide (0.0826 mole) were dissolved in 50% isopropyl alcohol (200 ml). Propargyl bromide (0.0826 mole) was added and the solution was heated to reflux for 6 hours. The solution was then cooled and the isopropyl alcohol was removed under vacuum. The residue was taken up in methylene chloride (200 ml), washed with water (200 ml), saturated sodium bicarbonate, saline and dried over magnesium sulfate. Removal of the solvent yielded crude product, which was recrystallized, from $CCl_4$ to give the pure product. (64.3% yield) m.p. 144–145° C.

EXAMPLE 5

2,4-Hexadienyl-4-Hydroxybenzoate p-Hydroxybenzoic acid (0.0724 mole) and 2,4-hexadienyl alcohol (0.0796 mole) were dissolved in diethyl ether (100 ml). Dicyclohexylcarbamide (0.0796 mole) in diethyl ether (50 ml) was added and the solution was stirred for 6 hours. The solution was filtered and the diethyl ether was removed under vacuum. The residue was taken up in methylene chloride (200 ml), washed with water (200 ml), saturated sodium bicarbonate, saline and dried over magnesium sulfate. Removal of the solvent yielded crude product, which was recrystallized, from $CCl_4$ to give the pure propargylparaben. (55.3% yield) m.p. 65–67° C.

EXAMPLE 6

2,4-Hexadienyl-2,4-Dihydroxybenzoate 2,4-Dihydroxybenzoic acid (0.0649 mole) and 2,4-hexadienyl alcohol (0.0714 mole) were dissolved in diethyl ether (100 ml). Dicyclohexylcarbamide (0.0714 mole) in diethyl ether (50 ml) was added and the solution was stirred for 6 hours. The solution was filtered and the diethyl ether was removed under vacuum. The residue was taken up in methylene chloride (200 ml), washed with water (200 ml), saturated sodium bicarbonate, saline and dried over magnesium sulfate. Removal of the solvent yielded crude product, which was recrystallized, from $CCl_4$ to give the pure propargylparaben. (41.5% yield) m.p. 82–84° C.

TEST METHODS

Activity Test

The present hydroxy benzoates were prepared in an emulsion of the composition:

|  | % Wt. |
|---|---|
| Phase A | |
| Stearic Acid | 5.0 |
| Mineral Oil | 2.5 |
| Cetyl Alcohol | 1.0 |
| Lareth-5 and Ceteth-5 and Oleth-5 and Steareth-5 | 0.5 |
| Glycerol Monostearate and Polyoxyethylene Stearate | 1.5 |
| Phase B | |
| Deionized Water | 88.0 |
| Triethanolamine 99% | 1.0 |
| Phase C | |
| Preservative in amounts indicated in Tables I-V | |
| Phase D | |
| Citric Acid 30% aqueous solution | 0.6 |

The emulsion was prepared by separately mixing components in phase A and phase B at 75–80° C. for 15 minutes. The phases were then combined and mixed for another 10 minutes and cooled to 45° C. with stirring. Preservative was then added followed by citric acid to adjust pH to from abut 6.5 to 7.5. Stirring of the resulting mixture was continued until a temperature of 30° C. was reached.

The activity tests were carried out using the following microorganisms: *A. niger, B. cepacia, C. albicans, E. coli, P. aeruginosa* and *S. aureus*. 50 g aliquots of the test emulsion containing various amounts of the preservative admixture as reported in Tables I–V were inoculated with approximately $10^7$–$10^8$ of the test organisms. The test samples then were stirred to disperse the challenge inoculum. The samples were incubated and assayed at 48 hours, 7, 14, 21 and 28 days. The assays were performed on 1 g, of the test sample by serially diluting $10^3$ to $10^6$ of the original concentration. The plating medium for bacteria was Letheen agar and for fungi it was low pH Mycophil agar with Tween 20. Each plated sample was incubated for 48 hours at 37° C. for bacteria, 5 days at 25° C. for mold and 3 days at 25° C. for fungi. After incubation, readings of the number of colonies per milliliter (cfu/ml) were made results were determined, as reported in associated Tables IA–VA. At 21 days the test product was reinoculated with half of the original inoculum.

Propargyl 3,4-Dihydroxybenzoate - 0.5%

TABLE I

| | Inoculum | |
|---|---|---|
| Organism | 0 Hour | 21 Day |
| Mold - *A. niger* 16404 | 64000 | 4700000 |
| Gram + bacteria - *B. cepacia* 25416 | 590000 | 1440000 |
| Yeast - *C. albicans* 10231 | 900000 | 2000000 |
| Gram negative - *E. coli* 8739 | 43000 | 3100000 |
| Gram negative - *P. aeruginosa* 9027 | 1200000 | 2400000 |
| Gram positive - *S. aureus* 6538 | 1500000 | 2800000 |

TABLE IA

| Organism | 48 hr | 7 days | 14 days | 21 days | 28 days |
|---|---|---|---|---|---|
| *A. niger* 16404 | <10 | <10 | <10 | <10 | <10 |
| *B. cepacia* 25416 | <10 | <10 | <10 | <10 | <10 |
| *C. albicans* 10231 | <10 | <10 | <10 | <10 | <10 |
| *E. coli* 8739 | <10 | <10 | <10 | <10 | <10 |
| *P. aeruginosa* 9027 | <10 | <10 | <10 | <10 | <10 |
| *S. aureus* 6538 | <10 | <10 | <10 | <10 | <10 |

Propargyl 2,4-Dihydroxybenzoate - 0.2%

TABLE II

| | Inoculum | |
|---|---|---|
| Organism | 0 Hour | 21 Day |
| *A. niger* 16404 | 60000 | 600000 |
| *B. cepacia* 25416 | 110000 | 700000 |
| *C. albicans* 10231 | 130000 | 800000 |
| *E. coli* 8739 | 900000 | 3400000 |
| *P. aeruginosa* 9027 | 1000000 | 6000000 |
| *S. aureus* 6538 | 1200000 | 1000000 |

TABLE IIA

| Organism | 48 hr | 7 days | 14 days | 21 days | 28 days |
|---|---|---|---|---|---|
| A. niger 16404 | 3500 | <10 | <10 | <10 | <10 |
| B. cepacia 25416 | <10 | <10 | <10 | <10 | <10 |
| C. albicans 10231 | 540 | <10 | <10 | <10 | <10 |
| E. coli 8739 | <10 | <10 | <10 | <10 | <10 |
| P. aeruginosa 9027 | <10 | <10 | <10 | <10 | <10 |
| S. aureus 6538 | <10 | <10 | <10 | <10 | <10 |

Propargyl 3-Chloro-4-Hydroxybenzoate - 0.5%

TABLE III

| | Inoculum | |
|---|---|---|
| Organism | 0 Hour | 21 Day |
| A. niger 16404 | 45000 | 50000 |
| B. cepacia 25416 | 42000 | 10000 |
| C. albicans 10231 | 800000 | 1000000 |
| E. coli 8739 | 1500000 | 1600000 |
| P. aeruginosa 9027 | 2000000 | 3100000 |
| S. aureus 6538 | 1500000 | 240000 |

TABLE IIIA

| Organism | 48 hr | 7 days | 14 days | 21 days | 28 days |
|---|---|---|---|---|---|
| A. niger 16404 | 10000 | <10 | <10 | <10 | <10 |
| B. cepacia 25416 | >10$^6$ | <10$^6$ | <10$^6$ | <10$^6$ | <10$^6$ |
| C. albicans 10231 | 280000 | 370 | <10 | <10 | <10 |
| E. coli 8739 | 30 | <10 | <10 | <10 | <10 |
| P. aeruginosa 9027 | <10 | <10 | 80 | <10 | <10 |
| S. aureus 6538 | 9600 | <10 | <10 | <10 | <10 |

2,4-Hexadienyl-4-Hydroxybenzoate - 0.5%

TABLE IV

| | Inoculum | |
|---|---|---|
| Organism | 0 Hour | 21 Day |
| A. niger 16404 | 280000 | 50000 |
| B. cepacia 25416 | 1200000 | 10000 |
| C. albicans 10231 | 110000 | 1000000 |
| E. coli 8739 | 1500000 | 1600000 |
| P. aeruginosa 9027 | 2300000 | 3100000 |
| S. aureus 6538 | 1600000 | 240000 |

TABLE IVA

| Organism | 48 hr | 7 days | 14 days | 21 days | 28 days |
|---|---|---|---|---|---|
| A. niger 16404 | 4800 | <10 | <10 | <10 | <10 |
| B. cepacia 25416 | <10$^6$ | <10$^6$ | <10$^6$ | <10$^6$ | <10$^6$ |
| C. albicans 10231 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| S. aureus 6538 | <10 | <10 | <10 | <10 | <10 |

2,4-Hexadienyl-2,4-Hydroxybenzoate - 0.5%

TABLE V

| | Inoculum | |
|---|---|---|
| Organism | 0 Hour | 21 Day |
| A. niger 16404 | 280000 | 50000 |
| B. cepacia 25416 | 1200000 | 10000 |
| C. albicans 10231 | 1100000 | 1000000 |
| E. coli 8739 | 1500000 | 1600000 |
| P. aeruginosa 9027 | 2300000 | 3100000 |
| S. aureus 6538 | 1600000 | 240000 |

TABLE VA

| Organism | 48 hr | 7 days | 14 days | 21 days | 28 days |
|---|---|---|---|---|---|
| A. niger 16404 | 4200 | 30 | <10 | <10 | <10 |
| B. cepacia 25416 | <10$^6$ | <10$^6$ | <10$^6$ | <10$^6$ | <10$^6$ |
| C. albicans 10231 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| S. aureus 6538 | <10 | <10 | <10 | <10 | <10 |

PARTITION COEFFICIENTS

The partition coefficients of the hydroxybenzoates reported in Table VI were determined by the log of oil/water solubility of the individual benzoates. A greater water partitioning is indicated by a low log value.

TABLE VI

| Compound | Log P |
|---|---|
| Propargylparahydroxy benzoate | 2.21 |
| Propargyl 3,4-dihydroxybenzoate | 1.08 |
| Propargyl 2,4-dihydroxybenzoate | 2.33 |
| Propargyl 3-chloro-4-hydroxybenzoate | 2.85 |
| 2,4-Hexadienyl-4-hydroxybenzoate | 4.02 |
| 2,4-Hexadienyl-2,4-dihydroxybenzoate | 4.15 |
| 2,4-Hexadienyl-3,4-dihydroxybenzoate | 2.89 |
| Parahydroxy ethyl benzoate | 2.47 |
| Parahydroxy propyl benzoate | 3.04 |
| Parahydroxy butyl benzoate | 3.57 |

What is claimed is:

1. A composition containing a substance subject to attack by a microorganism or fungus and between about 0.001% and about 2% of an anti-microbial, fungicidal amount of a water soluble, lipophilic/hydrophilic hydroxy benzoate having the formula:

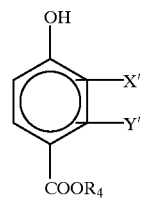

in which X' is hydrogen, halo, a $C_1$ to $C_6$ alkyl ether, or

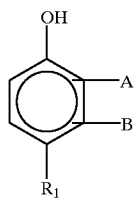

in which A is selected from the group of X';

B is selected from the group of Y' and $R_1$ is hydrogen, hydroxy, $C_1$ to $C_6$ alkyl, $C_1$ to $C_6$ alkoxy or —$COOR_2$ in which $R_2$ is $C_1$ to $C_6$ alkyl, a $C_2$ to $C_6$ olefinically unsaturated hydrocarbon radical or a $C_2$ to $C_7$ acetylenically unsaturated hydrocarbon radical, Y' is hydrogen, hydroxy, halo, a $C_1$ to $C_6$ alkyl or a $C_2$ to $C_6$ alkyl ether and $R_4$ is a lipophilic radical selected from the group of a $C_2$ to $C_7$ mono- or di-acetylenically unsaturated hydrocarbon radical or a mixture of said hydroxybenzoates and wherein the lipophilic/hydrophilic character of the hydroxybenzoate is balanced between the lipophilic character of the $R_4$ radical and the remaining substituents on the benzoate ring.

2. The hydroxybenzoate of claim 1 wherein X' is chlorine or hydroxy.

3. The composition of claim 1 wherein the composition contains between about 0.1 and about 1% of said hydroxybenzoate.

4. The composition of claim 1 wherein $R_4$ is a $C_2$ to $C_4$ monoacetylenically unsaturated radical and X is hydroxy.

5. The composition of claim 4 wherein $R_4$ is propargyl and Y is hydroxy.

6. The composition of claim 1 wherein said substance is an agrichemical.

7. The composition of claim 1 wherein said substance is an aqueous pesticidal, fungicidal formulation.

8. The composition of claim 1 wherein said substance is a topically applied cosmetic or pharmaceutical formulation.

9. The composition of claim 1 wherein said substance is a hair or skin care formulation.

10. The composition of claim 3 wherein said substance is a food or beverage.

11. The composition of claim 10 wherein said substance is an alcoholic beverage.

12. The composition of claim 10 wherein said substance is a food.

13. The composition of claim 12 wherein said food is a bakery foodstuff.

14. The composition of claim 8 wherein Y' is chloro, X' is hydroxy or $C_2$ to $C_6$ alkyl ether and $R_4$ is a $C_2$ to $C_4$ acetylenically unsaturated radical.

* * * * *